US008317778B2

(12) United States Patent
Spaide

(10) Patent No.: US 8,317,778 B2
(45) Date of Patent: Nov. 27, 2012

(54) STEERABLE AND FLEXIBLY CURVED PROBES

(76) Inventor: Richard F. Spaide, New York, NY (US)

( * ) Notice: Subject to any disclaimer, the term of this patent is extended or adjusted under 35 U.S.C. 154(b) by 785 days.

(21) Appl. No.: 12/524,949

(22) PCT Filed: May 30, 2007

(86) PCT No.: PCT/US2007/069917
§ 371 (c)(1),
(2), (4) Date: Jul. 29, 2009

(87) PCT Pub. No.: WO2008/094278
PCT Pub. Date: Aug. 7, 2008

(65) Prior Publication Data
US 2009/0312750 A1      Dec. 17, 2009

Related U.S. Application Data

(60) Provisional application No. 60/887,921, filed on Feb. 2, 2007, provisional application No. 60/887,635, filed on Feb. 1, 2007.

(51) Int. Cl.
*A61B 18/18* (2006.01)
(52) U.S. Cl. ................................. 606/4; 606/2
(58) Field of Classification Search ............... 606/2, 4–6
See application file for complete search history.

(56) References Cited

U.S. PATENT DOCUMENTS

| 5,454,794 A | 10/1995 | Narciso et al. |
| 6,270,476 B1 | 8/2001 | Santoianni et al. |
| 2005/0228452 A1 | 10/2005 | Mourlas et al. |
| 2006/0004348 A1* | 1/2006 | Scheller et al. ................... 606/4 |

FOREIGN PATENT DOCUMENTS

| WO | WO 92/10142 A1 | 6/1992 |
| WO | WO 2004/091380 A2 | 10/2004 |

* cited by examiner

*Primary Examiner* — William Choi
(74) *Attorney, Agent, or Firm* — Ronald Abramson; Hughes Hubbard & Reed LLP

(57) ABSTRACT

Steerable and flexibly curved probes are provided, primarily for A surgical applications. A probe with flexible distal portion is inserted through an incision or cannula and the flexible distal portion may be selectively bent or steered using a guide wire. The guide wire is extended through the probe on a radially offset axis, and affixed at its distal end to the distal end of the flexible distal portion. The curvature of the nitinol wire is induced by extending or retracting the wire from the proximal end of the flexible distal portion while the distal end of the guide wire remains affixed to the distal end of the probe. The guide wire is activated by a finger-actuated mechanism. A further embodiment is provided in which the guide wire is fixed at both ends of the flexible distal portion of the probe and has a normally curved conformation, and assumes such conformation after insertion through a straight cannula. Other embodiments and applications are similarly disclosed.

48 Claims, 13 Drawing Sheets

A

STEERABLE AND FLEXIBLY CURVED PROBES

CROSS-REFERENCE TO RELATED APPLICATIONS

This application is a national stage entry under 35 U.S.C. §371 of PCT/US07/69917, and further claims the priority and benefit of the respective filing dates of U.S. Provisional Application No. 60/887,635 ("Steer-able Intraocular Laser"), filed Feb. 1, 2007, and U.S. Provisional Application No. 60/887,921 ("Flexible Curved Intraocular Laser Probe"), filed Feb. 2, 2007, the entire respective disclosures of each of which provisional patent applications are hereby incorporated by reference herein.

BACKGROUND OF THE INVENTION

1. Field of the Invention

The invention concerns insertable probes, primarily in the surgical field, which can be steered or redirected after insertion. Several embodiments of the invention are in the form of steerable or flexibly curved microsurgical laser probes for use primarily in ophthalmic surgery. However, the invention also relates to insertable probes generally and has non-medical applications, for example, to non-medical endoscopy and boroscopy.

2. Background of the Related Art

A wide variety of surgical and diagnostic methods involve the insertion of probes, catheters, endoscopes and other devices into interior spaces and passageways within human or animal organs.

In the ophthalmic field, for example, intraocular laser photocoagulation, or the process of forming a blood clot in the interior of the eye using a laser, is performed in many types of surgical procedures. Application of laser photocoagulation is commonly done with the aid of a probe that carries an optical fiber that can direct the laser light. The fiber optic directs the laser energy from the laser source into the eye to the site of the coagulation. A typical prior art laser probe is shown in FIG. 1. Prior art probe 101 has a straight intraocular section 102 made from a straight metal sleeve. The metal sleeve covers the fiber optic 103 to protect the fiber optic 103. The guided laser output 104 exits the distal end 105 of the fiber optic 103 and impinges upon the coagulation site 106. Blood at the coagulation site 106 is coagulated by the energy transferred to that site by guided laser output 104.

Although easy to manufacture, there are shortcomings associated with the prior art laser probe. Surgical requirements limit how a laser probe 101 of the prior art can be inserted into the eye. When a laser probe 101 is inserted around insertion site 107 of the eye, the guided output 104 from the laser probe 101 cannot reach far periphery area 108 of the eye because the crystalline lens 109 of the eye blocks the range of motion of the laser probe 101. In fact, the furthest peripheral point toward the lens that the prior art laser probe 101 can reach is coagulation site 106 as shown in FIG. 1, when the probe comes into contact with the crystalline lens 109 at contact point 110. In addition to this limitation in reach, the laser probe 101 has an additional limitation that when the laser probe 101 is inserted at angle 111 as shown in FIG. 1, the intensity of the guided laser output 104 is reduced at coagulation site 106 because the guided laser output 104 is impinging on the coagulation site at a non-perpendicular angle 111. This reduction in intensity in turn reduces the effectiveness of the prior art laser probe 101. If, on the other hand, the guided laser output 104 could be made to be normal to the coagulation site 106, then the intensity of the guided laser output 104 would be at its maximum (for any given distance between distal end 105 and coagulation site 106) and the laser probe would be more effective.

In attempts to overcome these shortcomings, several variations of the metal sleeve laser probe of the prior art are in the field. There are curved laser probes made with a fixed and curved metal outer sleeve. These types of probes solve the problem of letting its guided laser output reach the far periphery of the eye. But unfortunately these probes can be used only with great difficulty in modern small incision vitrectomy surgery using cannulae. The cannulae used in vitrectomy surgery are typically straight cannulae that limit the passage of any curved probe or instrument. Even if the surgeon manages to force a curved laser probe through the cannula, the removal of the curved probe from the eye often causes the undesired effect of the cannula being removed from the eye as well. Another variation of the prior art laser probe uses a straight metal sleeve surrounding a fiber optic contained in a second metal tube having a curved contour. During surgery the outer sleeve is retracted allowing the inner sleeve to adopt a curved contour. But again, this type of laser probe is difficult to manipulate during surgery. There are additional shortcomings with this type of laser probe. For one example, it can curve in only one direction. For a second example, to remove the probe from the eye, the second metal tube must be manually straightened, necessitating awkward motions on the part of the surgeon and placing the eye at risk of inadvertent injury.

Another shortcoming common to all three types of prior art laser probes described above is that all of these laser probes employ a rigid metal outer sleeve that is potentially traumatic to delicate intraocular structures. Inadvertent contact with the lens or retina in particular can lead to serious physiological consequences.

Accordingly, the current state of intraocular laser probes is suboptimal and there is a need for a laser probe in which the angle or curvature of the optical fiber can be easily and quickly varied by the surgeon at will. Moreover, a device that solves the problems described above would have applicability in many other types of surgical and diagnostic procedures which involve the insertion of probes and the like into interior spaces and passageways within body organs of humans or animals, as well as corresponding non-medical mechanical applications.

SUMMARY OF THE INVENTION

The present invention addresses the above-noted shortcomings in the prior art by providing a steerable or flexibly curved instrument. In one embodiment, the instrument may be a probe that can be straight in its alignment while being inserted, such as through a cannula, but after insertion can adopt a curved shape upon manipulation by the operator so as to afford better access to interior areas that were not easily reached by a prior art devices.

In one embodiment, the probe comprises a tubular member providing an implement, for example, a surgical or diagnostic tool, at the distal end thereof. The tubular member is flexible along its axis and has at least one axial bore. A guide wire is disposed within the bore, such that the axis of the guide wire is radially offset from the axis of the tubular member. The guide wire is affixed to the tubular member at or near its distal end. The guide wire may be of a type, such as a nitinol wire, normally having a first lengthwise conformation (e.g., straight), and the property whereby it tends to return to said first lengthwise conformation after being deformed therefrom. In one embodiment, a fiber optic guiding the output of a laser source is also housed in the tubular member, so that the laser light exits the steerable probe at its distal end. Any other suitably sized implements, such as tools for performing a surgical operation, electrodes, sensors, imaging elements, etc., may be provided within and/or at the distal end of the probe; the probe itself may be adapted to hold the desired implement at or near its distal end.

Since the guide wire is affixed to or near the distal end of the probe, retracting the guide wire within the bore tends to make the probe curvedly deform in a transverse direction, such that (as a result of the radial offset of the guide wire as it runs through the tubular member) the guide wire will be situated on the inside of the radius of curvature of the probe (where the circumference is shorter). Similarly, extending the guide wire will tend to make the probe curvedly deform transversely in the opposite direction, i.e., such that the guide wire will be situated on the outside of the radius of curvature of the probe (where the circumference is longer). Thus, acting on the guide wire to extend or retract it in the bore provides a means of "steering" the probe.

In some embodiments, the radial offset of the guide wire within the tubular member is provided by having a separate, offset bore within the tubular member, for the guide wire. In other embodiments (for example small-gauge embodiments), the guide wire is radially offset but housed in the same bore as the optical fiber or other instrumentation fibers, cables or components (if any).

In other embodiments, a finger-actuated control within the handle actuates the slidable movement of the guide wire relative to the bore of the probe. Several possible embodiments of such a control are illustrated. In addition, various handle components are provided to hold the instrument and house the actuation controls.

In a further embodiment, the guide wire is provided in a normally curved (as opposed to straight) configuration, and is not slidably movable, but rather is fixed at both ends of the flexible tubular member. In this embodiment, the probe may, for example, be inserted through a straight cannula, by using minimal insertion force to transiently straighten it, and will then assume its naturally curved conformation after insertion, thus providing many of the advantages of the invention with a simpler apparatus than the other embodiments.

Further features and embodiments of the invention are illustrated by the accompanying drawings and further explained in the detailed description that follows.

DETAILED DESCRIPTION

The following is a description of several embodiments of various aspects of the invention. These embodiments are illustrative only. The invention is limited only by the scope of the claims that are appended hereto, and is by no means limited to particular examples described below.

The present invention is useful for many purposes. The anticipated field of use is generally referred to herein as "surgery." However, the terms "surgery" and "surgical" should be understood in a broad sense, as also including diagnostic methods carried out internally, and related instruments, as well as minimally invasive procedures and instruments, or those employed through a small incision, such as in connection with catheterization and endoscopy. In addition, the invention is also adaptable to non-medical applications, such as non-medical endoscopy and boroscopy, and the use of the term "surgical" or like medical-related terms should not be understood as limiting the scope of the invention to medical applications.

Figure 1:
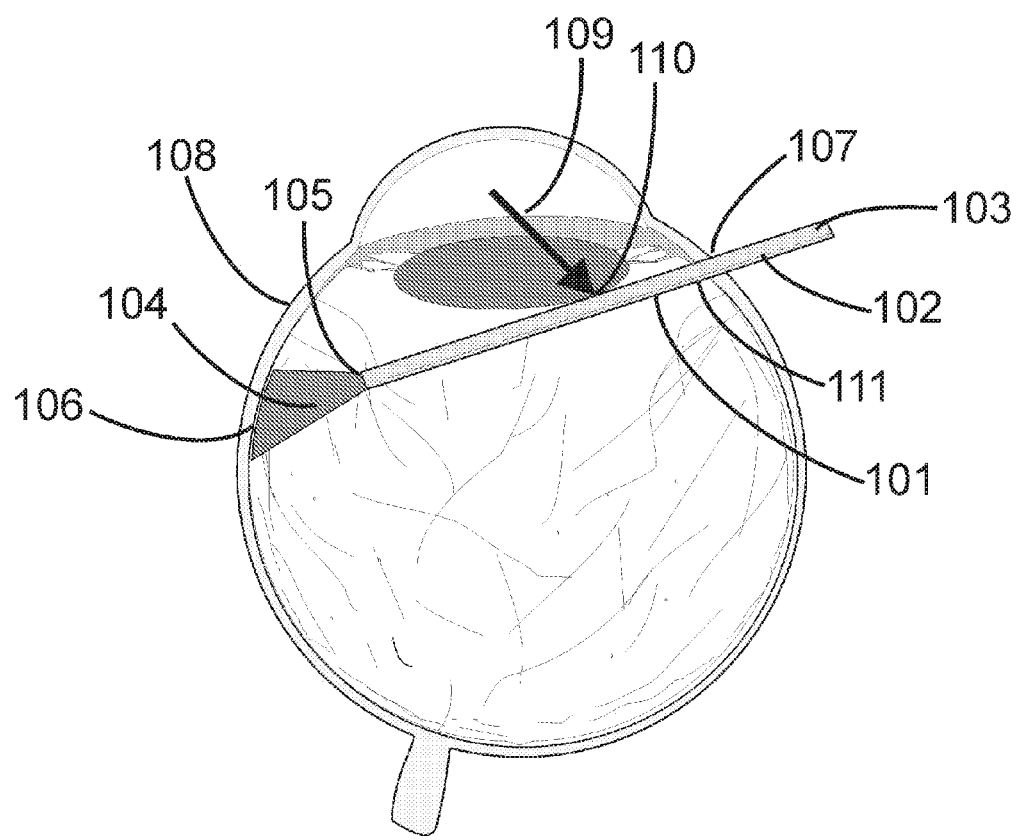
FIG. 1 is a side sectional view of a prior art laser probe while performing a coagulation operation in the eye.
Figure 2:
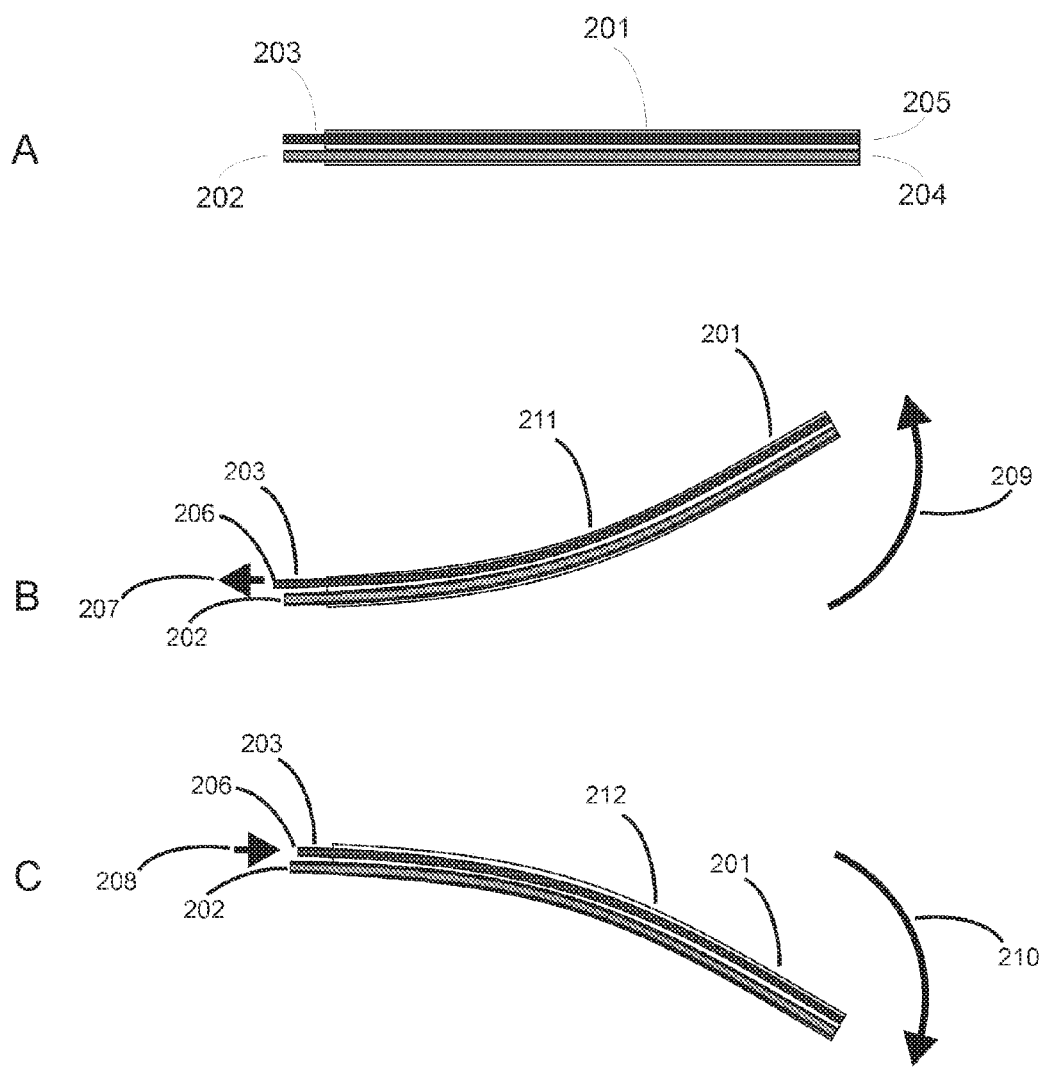
FIGS. 2A-C are three side sectional views of an embodiment of a probe in accordance with the present invention.

FIGS. 2A-C show side sectional views of an embodiment of a probe of the present invention and its steering action. As shown in FIG. 2A, the steerable probe has a tubular member 201 with an axial bore 205. The tubular member 201 is preferably made of a compressible substance to reduce the harm that may be caused by any inadvertent contact with any intraocular structures. Thus, tubular member 201 may be composed of many different types of materials, such as a variety of polymeric materials. Preferably, the material used for tubular member 201 should have the properties of being resilient, being very flexible, having low hysteresis, and that it can be precisely extruded. In one embodiment, tubular member 201 is composed from a PEBAX polymer, which is made from polyether block amides, a biocompatible, plasticizer free thermoplastic elastomer that has such properties. However, as PEBAX has proved difficult to secure with adhesives, PVC tubing, which has similar properties, is presently most preferred for tubular member 201.

An implement, for example a surgical or diagnostic tool, is situated at or near the distal end 204 of the tubular member 201. In the case of a steerable laser probe, optical fiber 202 is inserted lengthwise through the axial bore 205 of the tubular member 201 to provide a laser photocoagulator at distal end 204 (and in such a case, it will be understood that the distal end of the optical fiber, through which laser light is delivered, acts as the "implement"). Optical fiber 202 is typically comprised of a silica core with cladding and is preferably further coated with polyimide plastic coating to increase its resistance to breakage. (While this specification generally uses the term "optical fiber" to describe an optical conduit component in various embodiments, it will be understood that the term is intended to encompass any type of conduit, waveguide or fiber for transmitting electromagnetic energy, for example, multimode and singlemode fibers, as well as fiber optic cables comprised of a plurality of fibers.) Optical fiber 202 is also flexible. A wire member, referred to in this embodiment as a guide wire (203) is also inserted lengthwise through the axial bore 205 of the tubular member 201. The guide wire 203 is affixed to the tubular member at or near distal end 204. The proximal ends of both the guide wire 203 and the optical fiber 202 extend beyond the proximal end of the tubular member 201. Preferably, the guide wire 203 is provided in a form such that it is normally in a straight conformation. However, the guide wire 203 is flexible so that when a bending force is applied to it, the wire 203 will curvedly deform and have a curvature in accordance with the force. Once the force is removed, the guide wire 203 will tend to spring back to its normal straight conformation.

In the embodiment described above, guide wire 203 is made of nitinol. However, guide wire 203 may be any type of wire member, that is, any generally lengthwise-extended structure made of any material that is bendably flexible and resistant to tensile and compressive stress, that can be formed into a wire or cable shape. In some applications, it is desirable that this material exhibit the property of tending to return to a first conformation after being deformed from that conformation, but this property is not essential in other applications (in some applications, a degree of hysteresis may in fact be desirable). A plastic optical fiber (or other similar fiber optic) can bend at the distal tip and can also serve as such a guide wire. The advantage of the fiber optic is that it can also be used to bring light into the eye. This would provide a lighted laser probe. Treatments such as shaping the distal end of the fiber optic could help control the distribution of light emanating from the tip of the illumination fiber. Thus, the angular spread of light leaving the fiber optic delivering light could be different from the cone angle of laser light leaving the laser fiber optic. A fiber delivering light can be of the same composition as the laser fiber, namely silica fiber with polyimide cladding. Silica fiber with polyamide cladding costs much more per meter than does plastic optical fiber, and for simple delivery of light plastic optical fiber suffices. For purposes of this disclosure, and the claims, the term "wire member" is defined to include any structure as discussed in this paragraph.

The steering capability of the present invention is shown in FIGS. 2B-C. The guide wire 203 can slidably move with respect to the tubular member 201 in the axial direction when there is a force upon the guide wire 203 in the axial direction at the proximal end 206 of the wire 203. However, as explained above, the guide wire 203 is also fixed at or near the distal end 204 of tubular member 201. The slidable movement of the guide wire 203 at its proximal end 206 while being fixed at or near its distal end 204, held within a flexible housing, and with its longitudinal axis radially offset from the longitudinal axis of said housing, will cause the guide wire to curvedly deform such that the guide wire 203 becomes situated at either the inner or outer circumference of the bend when the force is applied—the inner circumference (which is shorter), when the force (207 in FIG. 2B) is to retract the guide wire 203, and the outer circumference (with is longer), when the force (208 in FIG. 2C) is to extend the guide wire 203.

To examine this action in further detail, we will refer again to FIG. 2B. In that figure, the force 207 that is pulling the guide wire 203 at the proximal end 206 causes the wire 203 to slidably move. But because the guide wire 203 is also fixed at or near distal end 204, the wire 203 in turn curvedly deforms in a transverse direction 209. Because the tubular member 201, and optical fiber 202 is flexible along its axis, it will curvedly deform along with the wire 203 in the transverse direction 209 so as to make the guide wire (which is radially offset within the bore 205) assume a position on the inner circumference 211 of the curved deformation. As shown in FIG. 2C, when a force 208 that pushes the guide wire 203 in the axial direction is exerted, so as to extend the guide wire 203 away axially from the proximate end of the device, the guide wire 203, along with the tubular member 201, will curvedly deform in the opposite transverse direction 210, so as to make the guide wire 203 assume a position on the outer circumference 212 of the curved deformation.

Thus, by exerting an axial force on wire 203, the slidable movement of the wire 203, coupled with its affixation at the distal end 204, creates a controllable transverse curved deformation of the guide wire 203 and tubular member 201. This curved deformation creates a range of steerable motion for distal end 204—wherein the precise location of the distal end 204 depends on the magnitude and direction of the forces 207 and 208. Furthermore, the proximal end of tubular member 201 may be kept straight while its distal end is being laterally moved. If inserted, for example through a cannula, the assembly may be rotated axially within the cannula (with the distal end also movable transversely, as above), to provide an additional degree of control to the instrument (and in addition, the distance of insertion can also be varied). Any implement, in one embodiment a laser photocoagulator, disposed at the distal end 204 of the instrument will be provided with a corresponding range of steerable motion.

Figure 3:
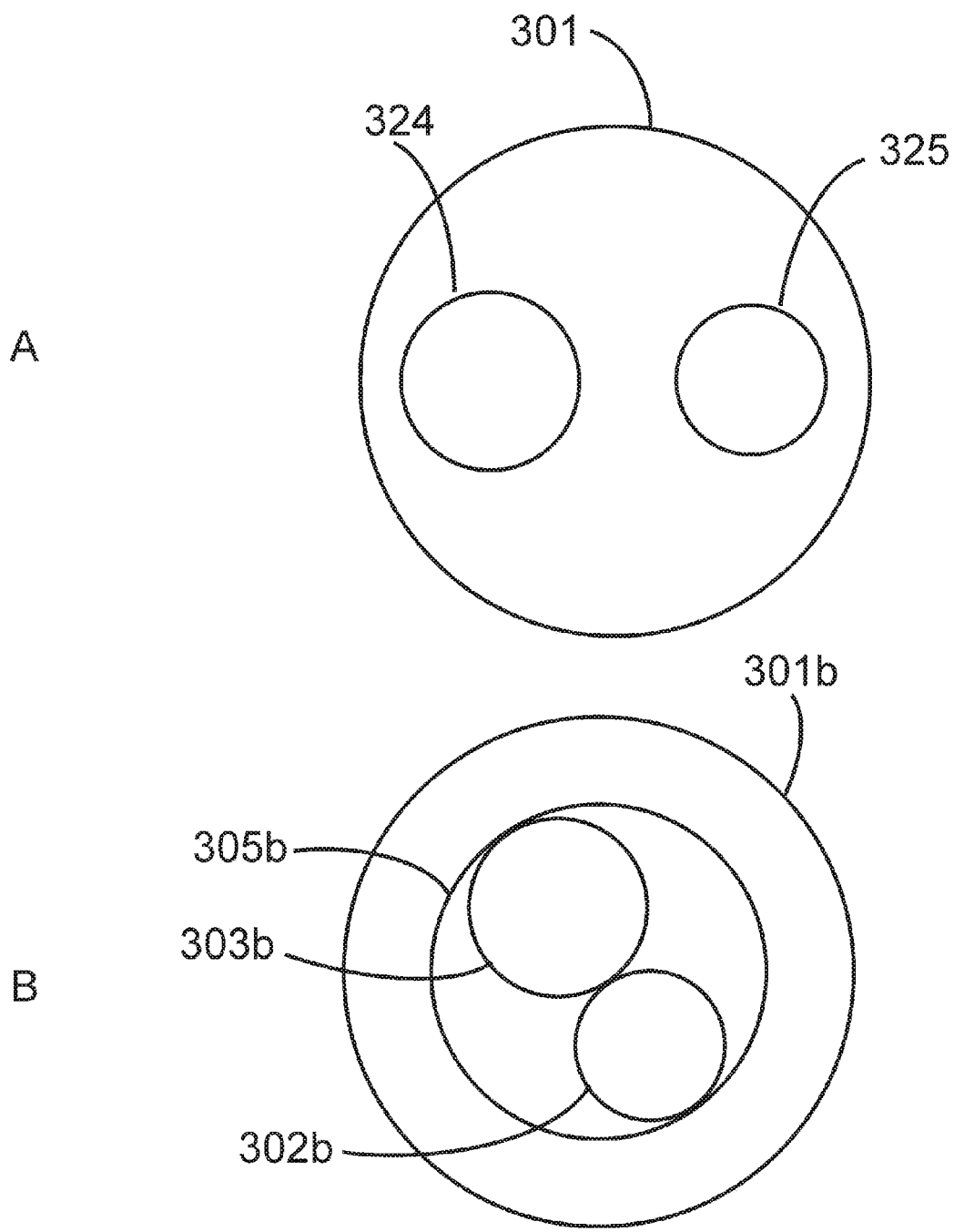
FIGS. 3A-B are cross-sectional views taken perpendicular to the axis of the tubular member of two different embodiments of a probe in accordance with the present invention.

FIGS. 3A-B are cross-sectional views of two embodiments of a probe of the present invention taken perpendicularly to the axis of tubular member 301 (similar to tubular member 201 of FIG. 2A). (It is noted that in this disclosure, the least two significant digits of reference numerals are used to denote functionally corresponding but not necessarily identical structures as among various drawings. These structures will be differentiated by the leading numeral in the "hundreds" place, and/or alternatively, by a trailing letter ("e", "f", "g" etc.) after the two least significant digits; thus, tubular member 301 in FIG. 3A functionally corresponds to tubular member 201 in FIG. 2A, and so forth.)

In FIG. 3A, tubular member 301 has two axial bores 314 and 325. Axial bores 324 (shown here as the larger of the two bores) and 325 (shown here as the smaller of the two bores) are off-center bores whose axes are (in one embodiment) parallel to, but radially offset from, the central axis of tubular member 301. In one embodiment, optical fiber 302 (similar to optical fiber 202 in FIG. 2A) extends lengthwise through axial bore 324, while guide wire 303 (similar to guide wire 203 in FIG. 2A) extends lengthwise through axial bore 325. In a preferred embodiment, guide wire 303 is made of nitinol and has a diameter of about 0.005 inches. In order to house a guide wire of such diameter, axial bore 325 has preferably a diameter of about 0.006 inches. Optical fiber having a core diameter of from about [50] microns to about 250 microns may be used. The optical fiber employed in this embodiment to comprise optical fiber 302 has a nominal diameter with cladding of about 100 to 120 microns, and the polyimide coating adds about 20 additional microns to the diameter. Thus, the total diameter of this optical fiber approaches 150 microns, or approximately 0.006 inches. In order to house such an optical fiber, axial bore 324 preferably has a diameter of about 0.007 inches.

A probe in accordance with the present invention, in numerous embodiments, can be used in vitrectomy surgery. Vitrectomy surgery can be performed with various sizes of instruments, for example, 20 gauge instruments, or 0.9 millimeter diameter, 23 gauge instruments, or 0.62 millimeter diameter, or 25 gauge instruments, or 0.5 millimeter diameter, or even smaller gauge instruments down to a diameter of about 0.25 mm. This means, for example, that in surgeries using 20 gauge instruments, the diameter of the tubular member cannot exceed about 0.9 millimeters. The twin axial bore configuration shown in FIG. 3A functions well for 20 and 23 gauge instruments, but for 25 gauge instruments, the diameter of the tubular member is too small for the twin bore configuration to be manufactured easily. This is addressed in the alternate embodiment shown in FIG. 3B.

In FIG. 3B, there is a single axial bore 305b in the tubular member 301b. Axial bore 305b and tubular member 301b are (in this embodiment) co-axial. Axial bore 305b is of a sufficient diameter so that both the guide wire, as shown in cross section 303b and the optical fiber, as shown in cross section 302b can extend lengthwise in the bore 305b. Note that in this configuration, the axes of both the guide wire and the optical fiber are parallel to the axis of the tubular member 301b but the axes do not coincide, and most particularly, the axis of guide wire 303b is radially offset from the axis of the tubular member, even though it runs within a bore that is coaxial with the tubular member. Thus, the mechanics of transverse curved deformation are qualitatively similar to those applicable to the dual bore embodiment when forces are applied to extend or retract the guide wire 303b relative to tubular member 301b. Accordingly, the single-bore embodiment of FIG. 3B displays comparable steerable behavior to the dual-bore embodiment of FIG. 3A.

Figure 4:
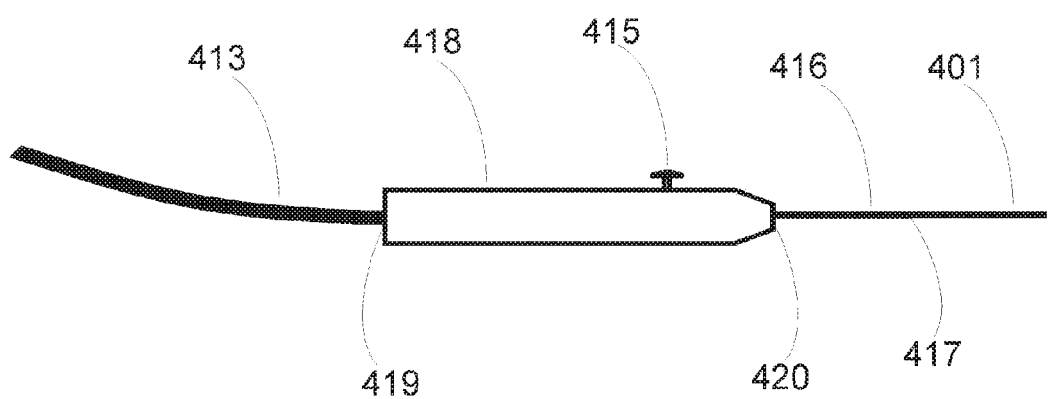
FIG. 4 is a side elevational view of an embodiment of a probe in accordance with the present invention coupled with an embodiment of a surgical handle in accordance with the present invention.

FIG. 4 is a side elevational view of an embodiment of a probe in accordance with the foregoing, coupled with an embodiment of a handle for the probe. Tubular member 401 (similar to tubular member 201 in FIG. 2A) is placed at the distal end 417 of a segment of rigid hollow tubing 416, preferably stainless steel hypodermic tubing, whose proximal end is in turn attached to a handle or boss 418. The rigid hollow tubing 416 can vary in diameter as required by the size of the surgical instruments used. Preferably, the diameter of the tubing 416 will correspond to the diameters of the cannulae or incisions employed in the various surgeries, for example vitrectomy surgery. The boss 418 also has an opening in the longitudinal (axial) direction (not visible in this drawing) from its distal end 420 to proximal end 419. An optical fiber 402 (similar to optical fiber 202 in FIG. 2A) and guide wire 403 (similar to guide wire 203 in FIG. 2A, but within the other components and therefore not shown in this drawing) run axially through tubular member 401, and extend past the proximal end 419 of the rigid hollow tubing 416, into the body of the boss 418 through its distal opening at 420. The optical fiber preferably extends past the proximal end 419 of the boss 418 so that it can be connected to an external laser source. Once outside the boss 418, the optical fiber may be covered by jacket 413. Guide wire 403, on the other hand, terminates within the boss 418 and is connected to an actuator 414 (not shown) internal to boss 418, which is controlled through finger pad 415. Movement of the finger pad 415 moves guide wire 403 through actuator 414, which causes the steering operation in this steerable probe embodiment. The structure of the actuator is the subject of several alternate designs, which are further described below with reference to FIGS. 5A-H.

First Actuator Embodiment

Figure 5:
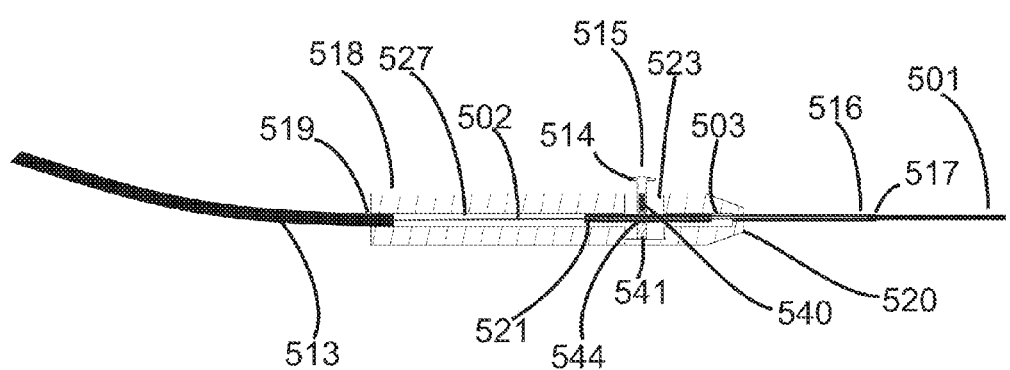
FIGS. 5A-B are side sectional views of a probe with a surgical handle, similar to the instrument shown in FIG. 4, and having a slidable finger-operated control.
FIGS. 5C-D are axial and transverse cross-sectional views, respectively, of the housing assembly within the finger-operated control shown in FIGS. 5A-B.
FIGS. 5E-F and 5G-H are, respectively, elevational views of two additional embodiments of a probe instrument having a finger-operated control, representing (in FIGS. 5E-F) a lever-based embodiment employing substantially the same housing assembly as in FIGS. 5A-B, and (in FIGS. 5G-H) an embodiment that has a different construction of the control.
Figure 5:
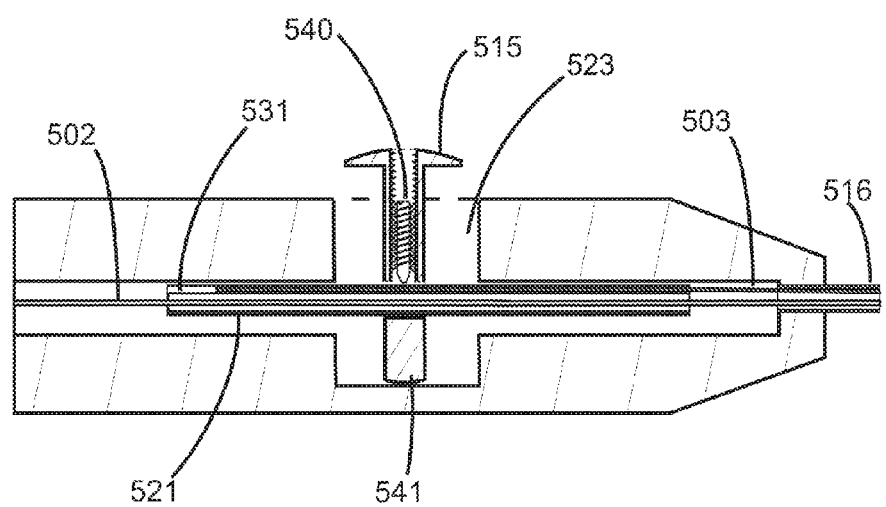
Figure 5:
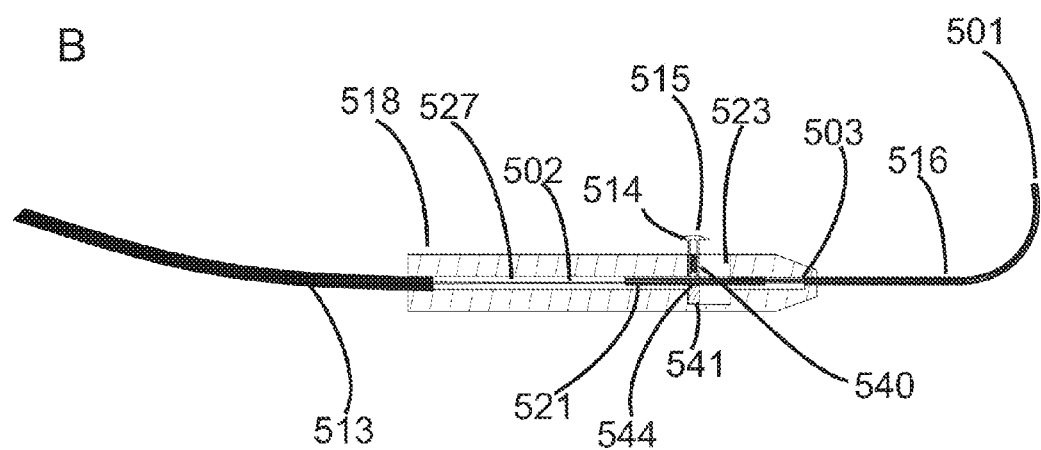
Figure 5:
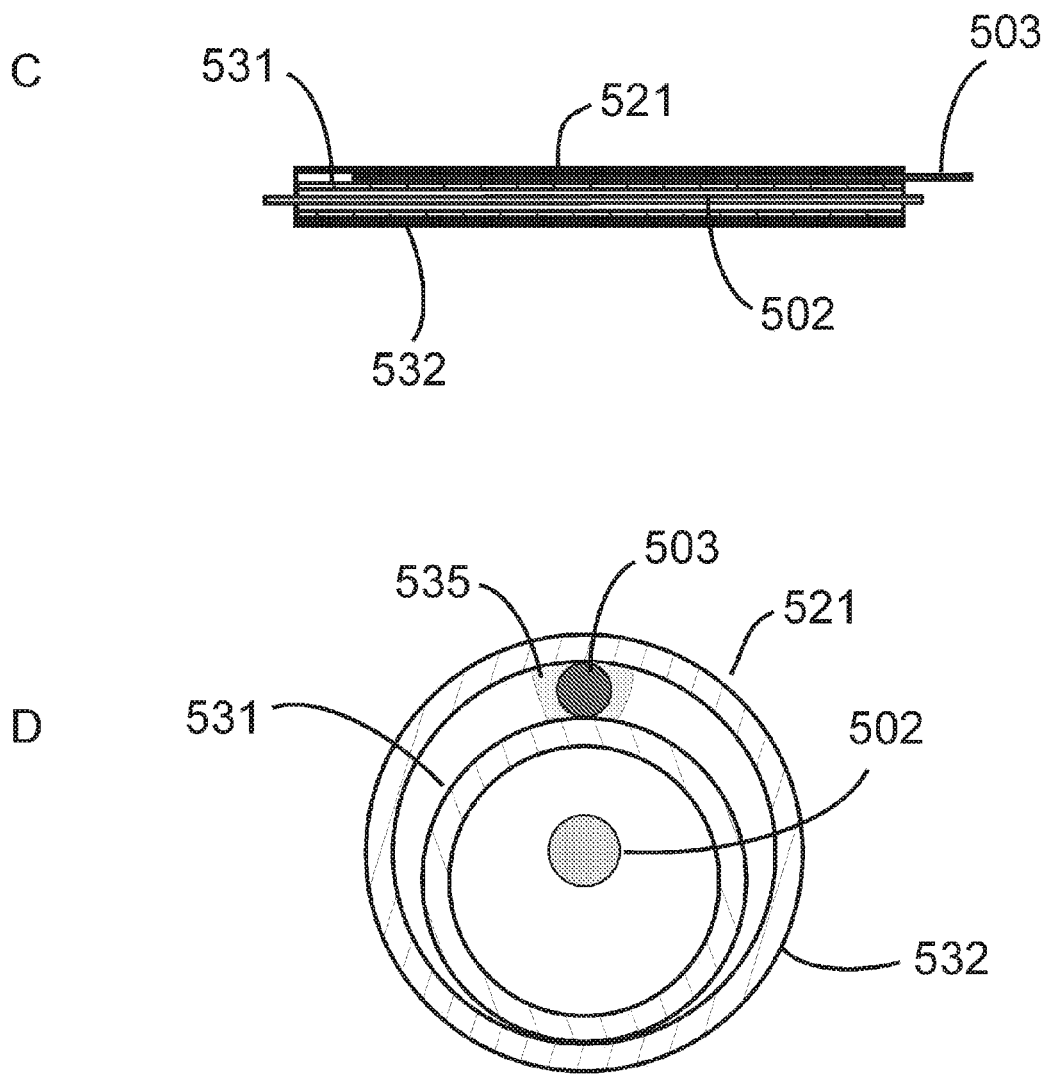
Figure 5:
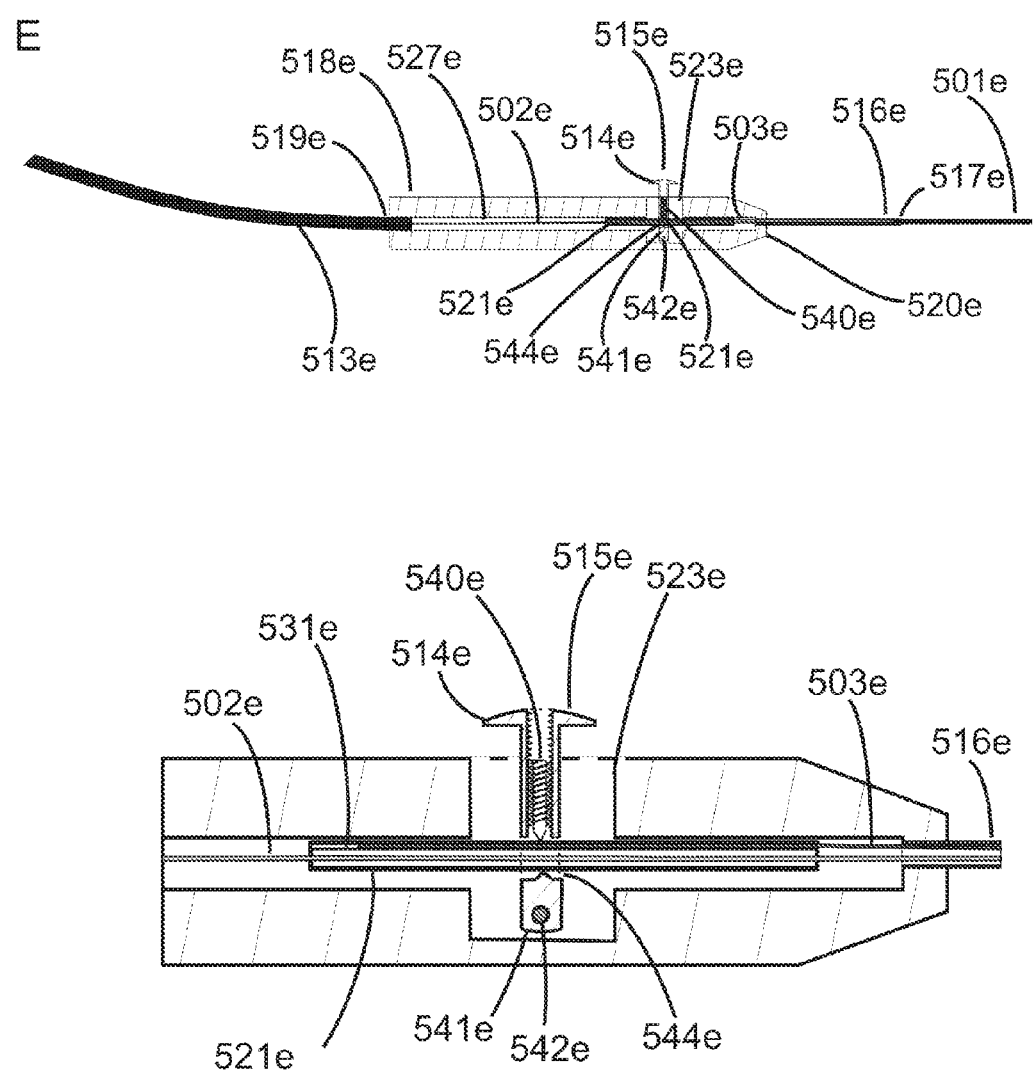
Figure 5:
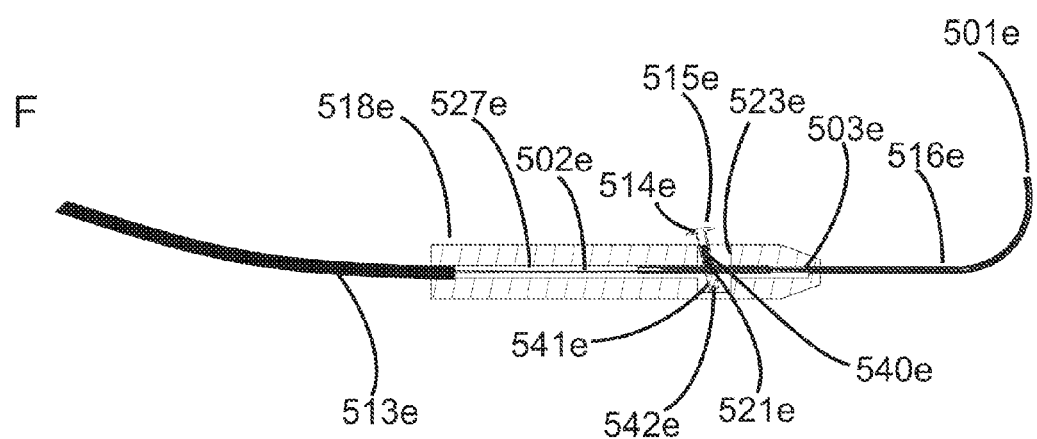
Figure 5:
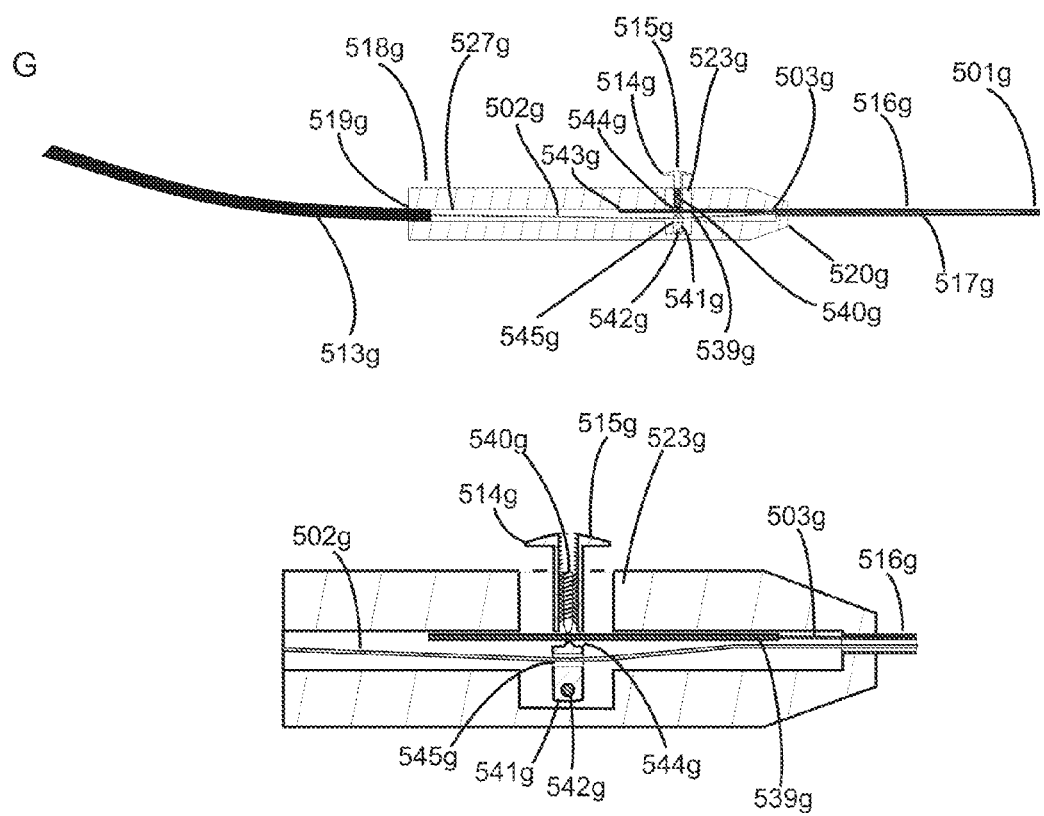
Figure 5:
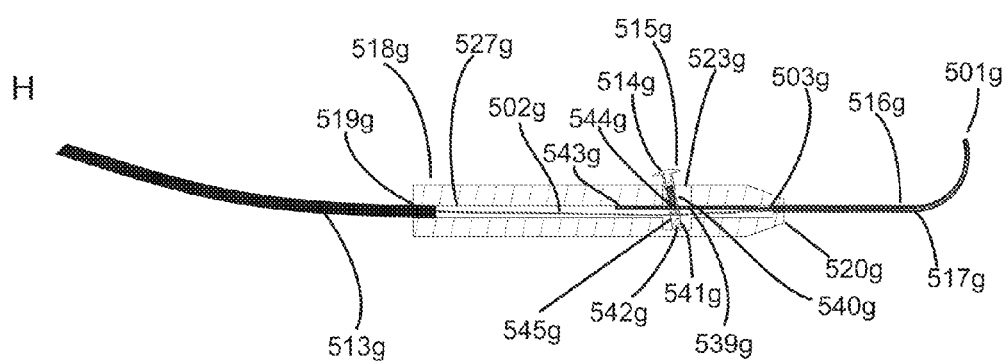

FIGS. 5A-B are side sectional views of what is currently the most preferred embodiment of the probe and handle combination as discussed above with respect to FIG. 4, showing its actuator structure 514. FIG. 5A shows that embodiment with finger pad 515 in a forward position, and FIG. 5B shows that embodiment with finger pad 515 in a rearward, retracted position. Finger pad 515 forms the top of a threaded shaft 540, which screws into a base receiving element 541. Base receiving element 541 has a transverse hole 544 through which housing 521 passes. Threaded shaft 540 is tightened in receiving element 541 in the manner of a set screw, so as to secure housing 521 to the assembly comprising receiving element 541, threaded shaft 540 and finger pad 515. Receiving element 541 is set in recess 523 so that it may slidably move fore and aft longitudinally within boss 518. The size of opening 523 is such that it limits the excursion of the finger pad mechanism so that harm to the laser fiber 502 will not occur. Housing 521 slidably fits into bore sections of axial bore 527 through boss 518, at the proximal and distal ends of recess 523. Sliding finger pad 515 forward and backward with respect to boss 518 moves housing 521 forward and backward within said bore sections, (correspondingly serving to extend and retract guide wire 503 as will be addressed below with respect to housing 521).

Housing 521 is shown in detail, in axial cross-section, in FIG. 5C, and in radial cross section in FIG. 5D. Outer housing tubing 532 is preferably 21 gauge extra thin wall stainless steel tubing, which typically has an inner diameter of 0.025 inches. Contained within this is inner housing tubing 531, which preferably is 25 gauge stainless steel tubing, which has an outside diameter of 0.020 inches. Wedged between the space caused by eccentric placement of 531 is guide wire 503. Additionally guide wire 503 is secured in place with adhesive 535. As shown in FIG. 5C, guide wire 503 terminates within housing 521. Laser fiber 502 is threaded lengthwise through inner housing tubing 531. In use, movement of the outer housing tubing 532 causes associated movement of guide wire 503 and inner housing tubing 531. The laser fiber 502 coursing through the center of inner housing tubing 531 is not attached to the tubing structure of housing 521, and not affected by the movement of that tubing structure. Thus, moving finger pad 415 fore and aft in recess 523 will extend and retract guide wire 503 relative to the proximal end 517 of tubular member 501, but will do so without affecting or putting any stress on laser fiber 502.

Second Actuator Embodiment

FIGS. 5E-F are side sectional views of an alternate embodiment of an actuator assembly for a probe and handle combination as discussed above with respect to FIG. 4. FIG. 5E shows the side sectional view of the probe and handle of such an embodiment at a first position. Axial bore 527e through the boss 518e is now visible. Also visible is a recess 523e in the boss 518e towards the distal end 520e of boss 518e. The recess 523e is used to accommodate actuator mechanism 514e. It is similar to recess 523 in FIG. 5A, but longer at the top to accommodate angular movement of the finger pad 515e. Axial bore 527e provides bore sections at either end of recess 523e. Actuator mechanism 514e has an input point n the form of finger pad 515e, through threaded shaft 540e which screws into receiving element 541e, which in turn has a fulcrum point 542e at its base. Housing 521e (similar in structure to housing 521 in FIG. 5A) passes through receiving element 541e through transverse hole 544e and is held in place by threaded shaft 540e by means of a detent (not shown) in housing 521e, which allows said housing to move fore and aft in the bore sections at either end of recess 523e. Thus, receiving element 541e is movably affixed to the boss 518e at fulcrum point 542e, so that receiving element 541e, threaded shaft 540e and finger pad 515e can be rocked fore and aft with respect to fulcrum point 542e in a plane approximately aligned with the distal probe portion of the instrument. Since housing 521e is driven by this assembly at a point intermediate the input element (finger pad 515e) and the fulcrum point 542e, a second class lever is thereby provided to control housing 521e and correspondingly, guide wire 503e. This way, when an input force is applied to finger pad 515e, such as when the surgeon pushes or pulls the finger pad 515e, receiving element 514e will move rotationally in the corresponding direction about the fulcrum point 542e, causing housing 521e to move fore and aft in the bore sections at either end of recess 523e, thereby moving guide wire 503e fore and aft relative to boss 518e and ultimately the proximal end of tubular member 501e. Guide wire 503e must be moved by only about +/−½ mm to flex the tip of the instrument, and thus, the amount of angular movement of the lever required to flex the tip is small.

Third Actuator Embodiment

In yet another actuator embodiment, as shown in FIGS. 5G and H, threaded shaft 540g is used to directly secure guide wire 503g to receiving element 541g. Guide wire 503g passes through a first transverse hole 544g in receiving element 541g and is held in place by threaded shaft 540g, acting as a set screw, while laser fiber 502g passes freely without attachment through a second transverse opening, transverse passage 545g, in receiving element 541g. Actuating this assembly through finger pad 515g again, as described with respect to FIG. 5E, rocks receiving element 541g as a second class lever with respect to fulcrum point 542g, thereby extending and retracting guide wire 503g to cause the bending action of tubular member 501g. Again, only a small rocking movement is required to flex the tip. In this embodiment, Guide wire 503g terminates inside boss 518g at proximal point 543g. Transverse passage 545g through receiving element 541g allows the optical fiber 502g to thread through and extend past the actuator assembly 514g, exit the boss 518g at the proximal end 519g and connect to an external laser source (not shown). This way, optical fiber 502g is not significantly moved or disturbed when the receiving element 541g rotates about the fulcrum point 542g.

A further feature is provided with respect to this third actuator embodiment. Due to the length of the guide wire 503g from the distal end of the boss 518g, at 520g, to the point of affixation to receiving member 541g, guide wire 503g may buckle in this span. This creates a problem because if guide wire 503g buckles in this span, then the levered rotation of receiving element 541g will not cause the guide wire 503g to slidably extend or retract, and in turn the guide wire 503g will not curvedly deform the tubular member 501g as desired. The solution to this problem is to house the guide wire 503g in hollow reinforcement tubing 531. The reinforcement tubing 531 is also held by compression by threaded shaft 540g, acting as a set screw in receiving element 541g. Because curvedly deforming the guide wire 503g within tubular member 50g by the operation of actuator 414g does not require much force, there is no significant bending moment in the reinforcement tubing 531.

In each of the above-described actuation embodiments (referring to FIG. 5A by way of example, though the following discussion applies equally to FIGS. 5E and 5G), causing guide wire 503 to extend or retract relative to boss 518 serves to actuate the bending motion of tubular member 501. Since the guide wire 503 is affixed to the tubular member 501 at or near the distal end of tubular member 501, and tubular member 501 is itself affixed to rigid hollow tubing 516, the tubular member 501 cannot slide along with the guide wire 503. Instead, as discussed with respect to the embodiment shown in FIGS. 2A and 2B, the extension or retraction of guide wire 503 in these embodiments cause the tubular member 501 and guide wire 503 within it to curvedly deform transversely, such that the guide wire 503 is situated on the inside circumference of the curvedly deformed tubular member when retracted and on the outside circumference when extended.

As shown in FIG. 5B (and, correspondingly in FIGS. 5F and 5H), when finger pad 515 is pulled backwards, the guide wire 503 is retracted relative to tubular member 501. As can be seen in FIG. 5B (and, correspondingly in FIGS. 5F and 5H), by comparing its position with the position of optical fiber 502, the axis of the guide wire 503 is disposed so as to be offset radially, toward the top of the drawing relative to the longitudinal axis of the tubular member 501. Consequently, the distal end of the tubular member 501 curves upward in response to being so retracted (placing it on the inside, shorter circumference of the now curved tubular member). Similarly, pushing the finger pad 515 forward will in turn cause the distal end of the tubular member 501 to curve downward. It should also be noted that releasing finger pad 515 in any of the illustrated embodiments after the probe has been actuated causes it to return to the position corresponding to the normal configuration of guide wire 503.

Because a surgical or diagnostic instrument, such as the output end of a laser photocoagulator, is situated at or near the distal end of the tubular member 501, the instrument can be directed as the tubular member is steered as described above. As configured in this embodiment, the distal end of the tubular member 501 is capable of curving more than 100 degrees in each direction, allowing nearly complete laser photocoagulation of the retina by placing the instrument through one sclerotomy opening in the eye. Because (in this particular embodiment) the guide wire 503 was selected to be statically straight such that it will only deform when a force is applied to it, releasing the finger pad 515 causes the guide wire 503 and in turn the tubular member 501 automatically to straighten. This is advantageous because the natural straight position can be assumed when the instrument first enters the eye, as insertion of an object is easier if done normal to the surface. Also if a cannula system is used during the surgery, the steerable probe is more easily inserted if straight because the cannula is straight. Thus, when the surgeon is first inserting the steerable probe of the present invention into the eye or a cannula, he need not exert any forces upon finger pad 515. After the tubular member 501 is inserted into the eye, a surgeon, by operating finger pad 515, can steerably curve the tubular member 501 to avoid obstruction internal in the eye as the crystalline lens, and more precisely position the instrument.

Figure 6:
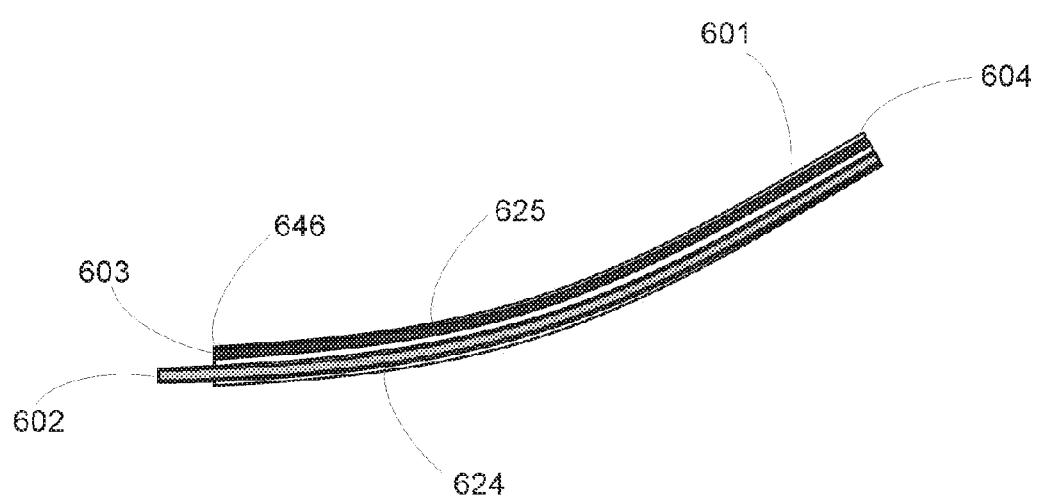
FIG. 6 is a side sectional view of an alternate embodiment of a probe in accordance with the present invention.

FIG. 6 shows another embodiment of a probe in accordance with the present invention. Instead of a dynamically steerable probe described above, the embodiment shown in FIG. 6 is a statically curved probe. Like the steerable probe, the statically curved probe has tubular member 601 having an axial bore 605 for housing a guide wire 603 and an implement (in this case the end of optical fiber 602) is attached to the distal end 604 of the tubular member 601. In the case of a curved laser probe, an optical fiber 602 is inserted lengthwise through the axial bore 605 of the tubular member 601 to provide a laser photocoagulator at distal end 604. Unlike the steerable probe however, the guide wire 603 is not statically straight but rather is trained to be curved. Because the tubular member 601 and optical fiber 602 are both flexible, they will also conform to this curvature. To avoid rotation by the guide wire 603 inside axial bore 605, the guide wire 603 is affixed to tubular member 601 at both distal end 604 and proximal end 606. The radius of curvature is large enough so that the curved probe can pass through a straight cannula with ease, thus overcoming limitations in the prior art. The preferred range of this radius is from approximately 15 mm to approximately 45 mm. The radius of curvature of the tubular member 601 in this embodiment is approximately 18 mm.

Figure 7:
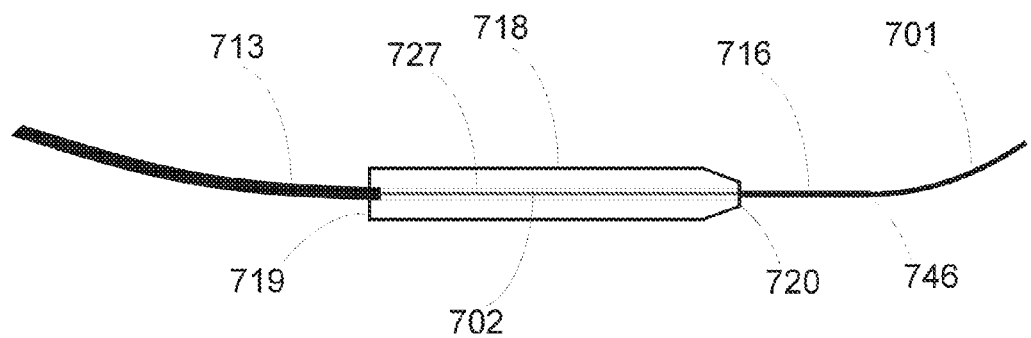
FIG. 7 is a side sectional view of a probe assembly comprising a handle and a probe as shown in FIG. 6.

FIG. 7 is a side sectional view of the probe embodiment described with respect to FIG. 6, coupled with a corresponding handle. The tubular member 601 containing the guide wire 603 (not shown in FIG. 7) and optical fiber 602 in the axial bore 605 (not shown) is attached at its proximal end 604 to the distal end of rigid hollow tubing 716, preferably stainless steel hypodermic tubing. The proximal end 720 of the hollow tubing 716 is in turn attached to a handle or boss 718. The rigid hollow tubing 716 can vary in diameter as required by the size of the surgical instruments used, and the diameter of the hollow tubing 716 corresponds to the diameters of the cannulae or incisions employed in the applicable surgical practice, for example vitrectomy surgery using various gauge equipment. The boss 718 also has an axial bore 727 in the longitudinal direction, running from its distal end 720 to proximal end 719. The optical fiber 602 extends through this bore past the proximal end 606 of the tubular member 601, through the hollow tubing 716, into and through the body of the boss 718 through its bore 727. The optical fiber 602 preferably extends past the proximal end 719 of the boss 718 so that it can be connected to an external laser source (not shown). Once outside the boss 718, the optical fiber 602 may be covered by jacket 713. The handle thus described allows the easy insertion of the probe through an incision or cannula. Once inserted, the probe assumes it naturally curved state, in which it can be selectively rotated into many positions, with better reach than a fully rigid probe.

Those skilled in the art will appreciate, upon reading the foregoing, that a probe in accordance with any of the embodiments of the present invention overcomes the limitations of the prior art. First, a probe in accordance with the present invention, either statically curved or dynamically steerably curved, can curve around internal obstructions such as the crystalline lens of the eye and allow the probe to have direct lines of access to all peripheral areas of the internal wall of the eye. Second, in case where the probe is used as a laser photocoagulator, by allowing the probe to have direct lines of access, the laser output emitting from the instrument can be directed to impinge upon the coagulation site of the eye at a normal angle of incidence, thus maximizing the intensity of the laser energy at the coagulation site. Third, unlike prior art probes that employ a rigid metal outer sleeve, the probes of the present invention employ a tubular member composed of a biocompatible, plasticizer free thermoplastic material, which may more safely be moved near delicate internal structures of the eye.

In addition, steerable and curved probes as described herein may be readily used and adapted for use in other types of surgical and diagnostic procedures, such as cardiovascular, gastrointestinal and other types of surgery and diagnostic methods in which it an instrument is introduced or threaded trough an opening or passageway and a mechanism is desirable to direct or steer the instrument after its introduction.

The foregoing summary, drawings, and detailed descriptions describe various embodiments of the invention and the principles by which the invention operates, and show the advantages that the invention provides over previous solutions. It is believed that the invention has been explained in sufficient detail to enable persons of ordinary skill in the field who study this disclosure to practice the techniques shown, as well as other variations and embodiments within the spirit of the invention that suit their individual needs. Accordingly, the specific features of the invention are not intended to limit the scope of the invention, as defined in the following claims.

I claim:

1. A steerable, flexible probe for use in ophthalmic surgery, to access areas of the retina that are inaccessible to straight probes, comprising:
   (a) a resilient tubular member adapted to access an intraocular surface, the tubular member having a proximal end, a distal end, and a first lumen therethrough, wherein said first lumen is axially offset from a longitudinal axis of said tubular member;
   (b) an elongated guide member having a proximal end and an opposing distal end, the elongated guide member disposed through said first lumen of said tubular member, wherein the elongated guide member is affixed to a distal section of said first lumen, and
   (c) a handle disposed at the proximal end of said tubular member, said handle comprising an actuator operatively engaged to said guide member, wherein said actuator is adapted to move said guide member between a first lengthwise conformation and a second lengthwise conformation thereof, and wherein said guide member tends to return to said first lengthwise conformation after being laterally deflected therefrom.

2. The steerable probe of claim 1 wherein said first lengthwise conformation is a generally straight conformation.

3. A method for performing an ophthalmic surgical or diagnostic procedure using a steerable probe assembly in accordance with claim 2, comprising
   (a) inserting an ophthalmic insertion cannula through a patient's sclera and into said patient's intraocular space;
   (b) inserting said probe assembly through said cannula,
   (c) actuating said guide member; to induce a desired curvature of said flexible tubular member of said probe;
   (d) rotating said probe about the its longitudinal axis to position said probe to a desired location;
   (e) deactuating said guide member such that said guide member resumes a substantially generally straight lengthwise conformation; and
   (f) removing said probe assembly from said cannula.

4. The steerable probe of claim 1 wherein said first lengthwise conformation is a conformation having a radius of curvature along a length of said guide member.

5. The steerable probe of claim 1 wherein said guide member may be laterally deflected from said first lengthwise conformation responsive to extension or retraction of said guide member relative to the proximal end of said first lumen.

6. The steerable probe of claim 5, wherein said handle is adapted to extend and retract said guide member relative to the proximal end of said lumen.

7. The steerable probe of claim 1, wherein said guide member is formed from shape memory material.

8. The steerable probe of claim 7, wherein said shape memory material is adapted to assume a generally straight lengthwise conformation in a temperature range including both room and body temperatures.

9. The steerable probe of claim 7, wherein said shape memory material is adapted to assume a conformation having a radius of curvature along a length of said guide member, in a temperature range including both room and body temperatures.

10. The steerable probe of claim 7, wherein said shape memory material is nickel-titanium alloy wire.

11. The steerable probe of claim 1, wherein said guide member comprises a material that transmits light.

12. The steerable probe of claim 11, wherein said guide member comprises a plastic optical fiber.

13. The steerable probe of claim 1, wherein said actuator slidingly operates said guide member.

14. The steerable probe of claim 1, wherein said actuator comprises a second class lever, the second class lever being proximally and distally moveable relative to said first lumen.

15. The steerable probe of claim 14, wherein said lever includes a lever bar, a fulcrum disposed in said handle, a finger-operable input element, and an output element on said lever bar attached to said guide member intermediate said finger-operable input element and said fulcrum.

16. The steerable probe of claim 15, wherein said guide member is compressively fastened to said lever bar.

17. The steerable probe of claim 16, further comprising a reinforcement tube disposed distal to said handle, wherein said reinforcement tube is disposed coaxially about at least a length of said guide member.

18. The steerable probe of claim 17, wherein said reinforcement tube has a length that extends to said lever and is secured to said lever bar by said compressive fastener.

19. The steerable probe of claim 1, further comprising a surgical or diagnostic implement disposed at or near the distal end of said first lumen.

20. The steerable probe of claim 19, wherein said surgical or diagnostic implement is an optical fiber, wherein the optical fiber has a length extending proximal to said handle and distal to said distal end of said tubular member.

21. The steerable probe of claim 20, wherein the steerable probe is a laser photocoagulator, and further wherein the laser photocoagulator comprises a laser light source coupled to the proximal end of said optical fiber.

22. The steerable probe of claim 21, wherein said optical fiber comprises silica optical fiber.

23. The steerable probe of claim 22, wherein said optical fiber is cladded and has a core diameter including cladding in a range of about 50 to 250 microns.

24. The steerable probe of claim 23 wherein said core diameter including cladding is about 100 to 120 microns.

25. The steerable probe of claim 22, wherein said cladding comprises a polyimide composition.

26. The steerable probe of claim 21, wherein said actuator is adapted to extend and retract said guide member relative to the proximal end of said first lumen, said actuator further comprises a second class lever moveable toward and away from said first lumen, having a lever bar, a fulcrum disposed in said handle, a finger-operable input element, and an output on said lever bar attached to said guide member intermediate said finger-operable input element and said fulcrum, and further wherein said optical fiber traverses said actuator through a passage mechanically isolated from the movement of said actuator.

27. The steerable probe of claim 26, wherein said passage is a passage through said lever bar.

28. The steerable probe claim 1, wherein the tubular member further comprises at least a second lumen in communication with a surgical or diagnostic implement.

29. The steerable probe of claim 28, wherein said guide member has an outer diameter of about 0.005 inches, said first lumen has a diameter of about 0.006 inches and said second lumen has a diameter of about 0.007 inches.

30. The steerable probe of claim 28, wherein an optical fiber is disposed in said second lumen.

31. The steerable probe of claim 30, wherein said actuator includes a passage, and further wherein said optical fiber traverses said passage.

32. The steerable probe of claim 31, wherein the passage is defined at a point generally intermediate said actuator.

33. The steerable probe of claim 31, wherein said actuator comprises a lever bar and said passage is a passage through said lever bar.

34. The steerable probe of claim 28, wherein said guide member is formed at least in part of an optical fiber.

35. The steerable probe of claim 34, wherein said guide member is a plastic optical fiber.

36. The steerable probe of claim 35, wherein the optical fiber carried in second lumen is a cladded silica optical fiber.

37. The steerable probe of claim 36, wherein the cladded silica optical fiber provides laser energy from said distal end of said tubular member and further wherein said plastic optical fiber provides illumination from said distal end of said tubular member.

38. The steerable probe of claim 1, wherein said tubular member has an outer diameter in a range from about 0.25 millimeters to about 0.9 millimeters.

39. The steerable probe of claim 1, wherein said tubular member is formed at least in part from a polymeric material.

40. The steerable probe of claim 39, wherein said polymeric material comprises PVC.

41. The steerable probe of claim 39, wherein said polymeric material comprises at least one polyether block amide.

42. A flexible probe for use in ophthalmic surgery to access areas of the retina that are inaccessible to straight probes, comprising:
   (a) a resilient tubular member adapted to access an intraocular surface, the tubular member having a proximal end, a distal end, and a first lumen therethrough;
   (b) an elongated, elastically deflectable guide member having a proximal end and an opposing distal end, the elongated guide member disposed through said first lumen, wherein the distal end of the elongated guide member is affixed to a distal section of said first lumen, the proximal end of the elongated guide member is affixed to a proximal section of said first lumen, and the elongated guide member is statically biased such that at least a distal portion thereof assumes a generally curved lengthwise conformation; and
   (c) a handle disposed at the proximal end of said tubular member such that a distal portion of said tubular member permanently extends away from said handle, said distal portion generally conforming in lengthwise shape to said generally curved lengthwise conformation of said distal portion of said guide member;
   wherein said tubular member may be elastically straightened by insertion into a cannula for passage therethrough, and will resume said generally curved lengthwise conformation after passing through said cannula.

43. The flexible probe of claim 42, wherein the radius of said curved conformation is in a range of 15-45 mm.

44. The flexible probe of claim 43, wherein said radius is approximately 18 mm.

45. The flexible probe of claim 42, further comprising an optical fiber extending proximally to said handle and distally to said distal end of said tubular member.

46. The flexible probe of claim 45, wherein said optical fiber is a cladded silica optical fiber, further comprising a laser light source coupled to the proximal end of said optical fiber.

47. The flexible probe of claim 42, further comprising a rigid sleeve covering a proximal portion of said flexible tubular member adjacent said handle, said rigid sleeve being shaped to be selectively insertable through an ophthalmic insertion cannula.

48. A method for performing an ophthalmic surgical or diagnostic procedure using a flexible probe in accordance with claim 42, comprising
   (a) inserting an ophthalmic insertion cannula through a patient's sclera and into said patient's intraocular space;
   (b) inserting said probe through said cannula to a sufficient insertion distance such that the tubular member emerges therefrom within the intraocular space and returns to said generally curved lengthwise conformation, and
   (c) rotating said probe about its longitudinal axis as may be necessary in order to point the distal end of said probe in the desired direction.

* * * * *